United States Patent
Itoh et al.

(10) Patent No.: US 8,329,930 B2
(45) Date of Patent: Dec. 11, 2012

(54) ALUMINUM COMPLEX AND USE THEREOF

(75) Inventors: Hisanori Itoh, Kanagawa (JP); Yoji Hori, Kanagawa (JP)

(73) Assignee: Takasago International Corporation, Tokyo (JP)

( * ) Notice: Subject to any disclaimer, the term of this patent is extended or adjusted under 35 U.S.C. 154(b) by 198 days.

(21) Appl. No.: 12/991,967

(22) PCT Filed: May 25, 2009

(86) PCT No.: PCT/JP2009/002279
§ 371 (c)(1),
(2), (4) Date: Dec. 8, 2010

(87) PCT Pub. No.: WO2009/144906
PCT Pub. Date: Dec. 3, 2009

(65) Prior Publication Data
US 2011/0082308 A1    Apr. 7, 2011

(30) Foreign Application Priority Data

May 26, 2008  (JP) .................................. 2008-137091

(51) Int. Cl.
*C07F 5/06* (2006.01)
*C07C 35/08* (2006.01)

(52) U.S. Cl. .......................... 556/170; 556/182; 568/828

(58) Field of Classification Search .................. 556/170, 556/182; 568/828
See application file for complete search history.

(56) References Cited

U.S. PATENT DOCUMENTS
6,258,960 B1    7/2001   Antilla et al.

FOREIGN PATENT DOCUMENTS
JP      1-230537        9/1989
WO      2005/014509     2/2005

OTHER PUBLICATIONS

Graves et al., Journal of Organic Chemistry, vol. 72, No. 24, pp. 9121-9133 (published on the Web Oct. 23, 2007).*
International Search Report issued Jul. 28, 2009 in International (PCT) Application No. PCT/JP2009/002279.
A. Sjoholm et al., "Investigation of Lewis Acid-Catalyzed Asymmetric Aza-Diels-Alder Reactions of 2H-Azirines", J. Org. Chem., vol. 68, No. 26, pp. 9958-9963, 2003.
K. Maruoka et al., "Asymmetric Hetero-Diels-Alder Reactions Catalyzed by Chiral Organoaluminum Reagent", J. Am. Chem., Soc., vol. 110, No. 1, pp. 310-312, 1988.
S. Sakane et al., Chiral Leaving Group: Asymmetric Synthesis of Limonene and Bisabolene, Tetrahedron, vol. 42, No. 8, pp. 2193-2201, 1986.
English translation of the International Preliminary Report on Patentability and Written Opinion dated Jan. 11, 2011.

* cited by examiner

*Primary Examiner* — Porfirio Nazario Gonzalez
(74) *Attorney, Agent, or Firm* — Wenderoth, Lind & Ponack, L.L.P.

(57) ABSTRACT

Provided is a process in which cyclization of a compound having, in a molecule, a formyl group and a double bond which allow carbonyl-ene cyclization, the compound existing as a mixture of optical isomers thereof, increases the ratio of a particular optical isomer not only in a cyclized compound, but also in an unreacted compound. The process comprises performing, in the presence of a specified aluminum complex represented by the general formula: $[Al_2(L^1)_n(L^2)_{3-n}]_m$, cyclization of a compound having, in a molecule, a formyl group and a double bond which allow carbonyl-ene cyclization, the compound existing as a mixture of optical isomers thereof, to increase the ratio of a particular optical isomer.

9 Claims, 2 Drawing Sheets

ALUMINUM COMPLEX AND USE THEREOF

This application is a U.S. national stage of International Application No. PCT/W2009/002279 filed May 25, 2009.

TECHNICAL FIELD

The present invention utilizes a novel chiral aluminum complex as a catalyst in cyclization of a compound having, in a molecule, a formyl group and a double bond which allow carbonyl-ene cyclization, the compound existing as a mixture of optical isomers thereof, and thereby increases the ratio of a particular optical isomer in a cyclized compound or an unreacted compound.

In particular, the present invention enables optical resolution of citronellal having a low enantiomeric excess ratio by allowing preferential cyclization of only one of two stereoisomers, resulting in an increased enantiomeric excess ratio, or enables production of enantioenriched isopulegol from the citronellal via selective cyclization.

BACKGROUND ART

Menthol, especially l-menthol, has been an extremely important refreshing flavor and been extensively used. As a synthesis process of menthol, optical resolution of dl-menthol and asymmetric synthesis are known (nonpatent literature 1). In the asymmetric synthesis of l-menthol, l-menthol is produced by hydrogenation of the precursor l-isopulegol. For synthesis of l-isopulegol, the selective cyclization of d-citronellal is an important step.

As the selective cyclization of d-citronellal, techniques which use zinc bromide or other reagents have long been known. In recent years, there are reports on highly selective cyclization using an aluminum complex as a catalyst. For example, highly selective cyclization which uses, as a catalyst, an aluminum complex having a 2,6-diphenylphenol-derived ligand was invented (patent literature 1). Since then, cyclization which uses an aluminum complex having a ligand derived from compounds having a phenolic hydroxyl group (patent literatures 2, 3 and 4), and cyclization which uses an aluminum complex having a silyl ether moiety (patent literature 5) have been reported. However, there is no report on selective cyclization of only one of the two stereoisomers in racemic citronellal using an optically active aluminum complex. Many aluminum complexes having a biaryldiol skeleton, which is an axially asymmetric ligand, have been reported, but among them, only a monovalent cationic hydride complex (patent literature 6) consists of aluminum and biaryldiol at the ratio of 2:3 (aluminum:biaryldiol).

CITATION LIST

Patent Literature

Patent Literature 1: JP-A 2002-212121
Patent Literature 2: WO 2006/069659
Patent Literature 3: WO 2006/092433
Patent Literature 4: DE 102005023953
Patent Literature 5: WO 2007/039342
Patent Literature 6: U.S. Pat. No. 6,090,950

Nonpatent Literature

Non Patent Literature 1:
Synthetic Flavor, Motoichi Indou, The Chemical Daily Co., Ltd. pp. 106-114

SUMMARY OF INVENTION

Technical Problem

An object of the present invention is to provide a process for obtaining an objective optically active alcohol or olefin aldehyde with a higher optical purity, the process comprising using a novel chiral aluminum complex as a catalyst in intramolecular carbonyl-ene cyclization to increase the ratio of a particular optical isomer in a cyclized compound or an unreacted compound. In particular, the present invention relates to a process for obtaining l-isopulegol and l-citronellal or d-isopulegol and d-citronellal by optical resolution of citronellal via highly selective cyclization.

Solution to Problem

The present inventors conducted extensive research to achieve the above-mentioned object. As a result, they found that use of, as a catalyst, an aluminum complex having an optically active biaryldiol as a ligand allows preferential cyclization of citronellal that fits the conformation of the chiral ligand, resulting in improvement in the dl-enantioselectivity, and that among four isomers, i.e., isopulegol, isoisopulegol, neoisopulegol and neoisoisopulegol, isopulegol can be produced in a highly selective manner and obtained at a high yield. Based on these findings, the present inventors completed the present invention. Also, the chiral ligand described above can be reused as a ligand of the aluminum catalyst by recovery from the reaction system after completion of the cyclization.

Namely, the present invention includes the contents of the following [1] to [10].

[1] An aluminum complex obtainable by a reaction of 1 Eq of an aluminum compound represented by the following general formula (1):

$$Al(Lg)_3 \qquad (1)$$

(in the formula (1), Lg represents an alkyl group, an alkoxy group or a halogen atom) and 1.5 Eq or more of a biaryldiol compound represented by the following general formula (2):

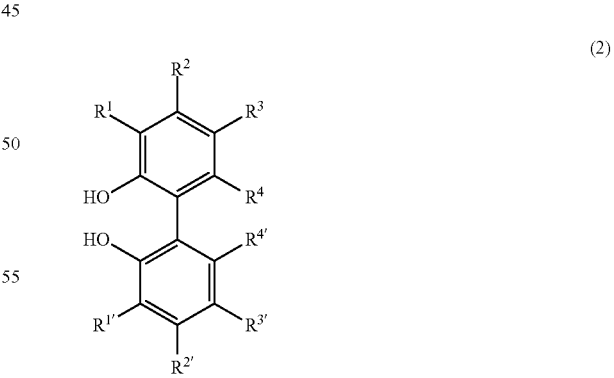

(2)

(in the formula (2), $R^1$, $R^2$, $R^3$, $R^{1'}$, $R^{2'}$ and $R^{3'}$ independently represent a hydrogen atom, a halogen atom, a hydroxyl group, a saturated or unsaturated carbon chain, an optionally substituted aryl group, an optionally substituted heterocyclic group, an alkoxy group, an aryloxy group, an aralkyloxy group, a carboxyl group which may be protected by a protecting group, an amino group, a substituted amino group, a nitro group, an acyl group, a substituted silyl group or a polymer chain; $R^4$ and $R^{4'}$ independently represent a hydroxyl group, a halogen atom, a saturated or unsaturated carbon chain, an optionally substituted aryl group, an optionally substituted heterocyclic group, an alkoxy group, an aryloxy group, an aralkyloxy group, a carboxyl group which may be protected by a protecting group, an amino group, a substituted amino group, an acyl group, a substituted silyl group or a nitro group; and $R^1$ and $R^2$, $R^2$ and $R^3$, $R^3$ and $R^4$, $R^4$ and $R^{4'}$, $R^{4'}$ and $R^{3'}$, $R^{3'}$ and $R^{2'}$, or $R^{2'}$ and $R^{1'}$ may bind to each other to form a ring), or by a reaction of 1 Eq of the aluminum compound represented by the above general formula (1), 1.1 to 1.3 Eq of the biaryldiol compound represented by the above general formula (2) and 0.4 Eq or more of a biaryldiol compound represented by the following general formula (3):

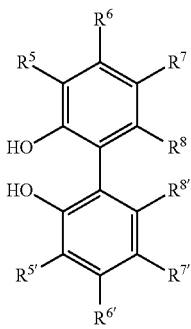

(3)

(in the formula (3), $R^5$, $R^6$, $R^7$, $R^8$, $R^{5'}$, $R^{6'}$, $R^{7'}$ and $R^{8'}$ independently represent a hydrogen atom, a hydroxyl group, a halogen atom, a saturated or unsaturated carbon chain, an optionally substituted aryl group, an optionally substituted heterocyclic group, an alkoxy group, an aryloxy group, an aralkyloxy group, a carboxyl group which may be protected by a protecting group, an amino group, a substituted amino group, a nitro group, an acyl group, a substituted silyl group or a polymer chain; and $R^5$ and $R^6$, $R^6$ and $R^7$, $R^7$ and $R^8$, $R^8$ and $R^{8'}$, $R^{8'}$ and $R^{7'}$, $R^{7'}$ and $R^{6'}$, or $R^{6'}$ and $R^{5'}$ may bind to each other to form a ring).

[2] The aluminum complex according to the above [1], wherein the biaryldiol compound represented by the general formula (2) is an optically active compound having a chiral axis.

[3] The aluminum complex according to the above [2], wherein both of the biaryldiol compound represented by the general formula (2) and the biaryldiol compound represented by the general formula (3) are optically active compounds having a chiral axis.

[4] The aluminum complex according to any of the above [1] to [3], which is represented by the following general formula (1'):

$[Al_2(L^1)_n(L^2)_{3-n}]_m$ (1')

(in the formula (1'), n represents an integer of 2 or 3; m represents a natural number; $L^1$ represents a ligand represented by the following formula (2'); and $L^2$ represents a ligand represented by the following formula (3'):

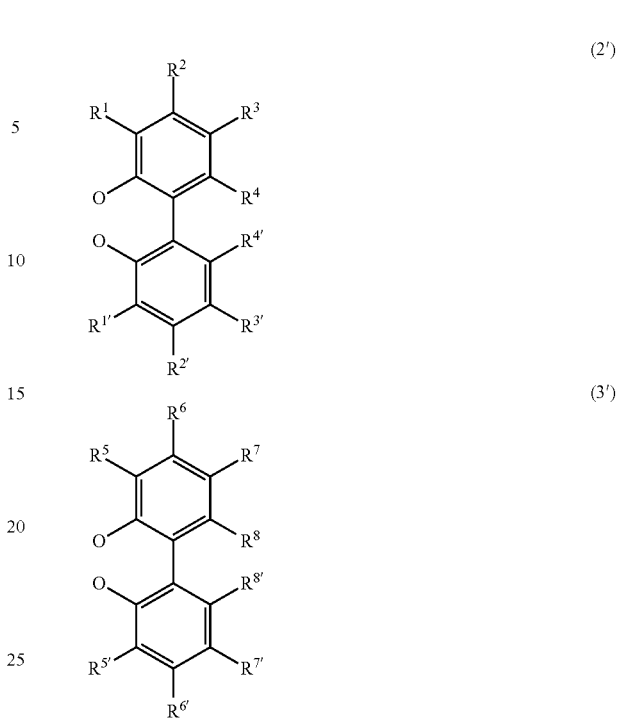

(in the formula (2'), $R^1$, $R^2$, $R^3$, $R^{1'}$, $R^{2'}$ and $R^{3'}$ independently represent a hydrogen atom, a halogen atom, a hydroxyl group, a saturated or unsaturated carbon chain, an optionally substituted aryl group, an optionally substituted heterocyclic group, an alkoxy group, an aryloxy group, an aralkyloxy group, a carboxyl group which may be protected by a protecting group, an amino group, a substituted amino group, a nitro group, an acyl group, a substituted silyl group or a polymer chain; $R^4$ and $R^{4'}$ independently represent a hydroxyl group, a halogen atom, a saturated or unsaturated carbon chain, an optionally substituted aryl group, an optionally substituted heterocyclic group, an alkoxy group, an aryloxy group, an aralkyloxy group, a carboxyl group which may be protected by a protecting group, an amino group, a substituted amino group, an acyl group, a substituted silyl group or a nitro group; and $R^1$ and $R^2$, $R^2$ and $R^3$, $R^3$ and $R^4$, $R^4$ and $R^{4'}$, $R^{4'}$ and $R^{3'}$, $R^{3'}$ and $R^{2'}$, or $R^{2'}$ and $R^{1'}$ may bind to each other to form a ring, and in the formula (3'), $R^5$, $R^6$, $R^7$, $R^8$, $R^{5'}$, $R^{6'}$, $R^{7'}$ and $R^{8'}$ independently represent a hydrogen atom, a hydroxyl group, a halogen atom, a saturated or unsaturated carbon chain, an optionally substituted aryl group, an optionally substituted heterocyclic group, an alkoxy group, an aryloxy group, an aralkyloxy group, a carboxyl group which may be protected by a protecting group, an amino group, a substituted amino group, a nitro group, an acyl group, a substituted silyl group or a polymer chain; and $R^5$ and $R^6$, $R^6$ and $R^7$, $R^7$ and $R^8$, $R^8$ and $R^{8'}$, $R^{8'}$ and $R^{7'}$, $R^{7'}$ and $R^{6'}$, or $R^{6'}$ and $R^{5'}$ may bind to each other to form a ring)).

[5] A process for preparing an optically active compound, comprising performing, in the presence of an aluminum complex, cyclization of a compound having, in a molecule, a formyl group and a double bond which allow carbonyl-ene cyclization, the compound existing as a mixture of optical isomers thereof, to increase the ratio of a particular optical isomer in a cyclized compound or an unreacted compound, the aluminum complex being obtainable by a reaction of 1 Eq of an aluminum compound represented by the following general formula (1):

$Al(Lg)_3$ (1)

(in the formula (1), Lg represents an alkyl group, an alkoxy group or a halogen atom) and 1.0 Eq or more of an optically active biaryldiol compound having a chiral axis represented by the following general formula (2):

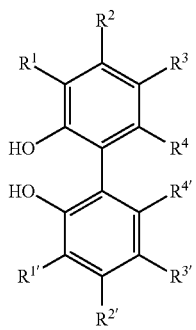

(2)

(in the formula (2), $R^1$, $R^2$, $R^3$, $R^{1'}$, $R^{2'}$ and $R^{3'}$ independently represent a hydrogen atom, a halogen atom, a hydroxyl group, a saturated or unsaturated carbon chain, an optionally substituted aryl group, an optionally substituted heterocyclic group, an alkoxy group, an aryloxy group, an aralkyloxy group, a carboxyl group which may be protected by a protecting group, an amino group, a substituted amino group, a nitro group, an acyl group, a substituted silyl group or a polymer chain; $R^4$ and $R^{4'}$ independently represent a hydroxyl group, a halogen atom, a saturated or unsaturated carbon chain, an optionally substituted aryl group, an optionally substituted heterocyclic group, an alkoxy group, an aryloxy group, an aralkyloxy group, a carboxyl group which may be protected by a protecting group, an amino group, a substituted amino group, an acyl group, a substituted silyl group or a nitro group; and $R^1$ and $R^2$, $R^2$ and $R^3$, $R^3$ and $R^4$, $R^4$ and $R^{4'}$, $R^{4'}$ and $R^{3'}$, $R^{3'}$ and $R^{2'}$, or $R^{2'}$ and $R^{1'}$ may bind to each other to form a ring), or
by a reaction of 1 Eq of the aluminum compound represented by the above general formula (1), 1.0 to 1.3 Eq of the optically active biaryldiol compound having a chiral axis represented by the above general formula (2) and 0.4 Eq or more of a biaryldiol compound represented by the following general formula (3):

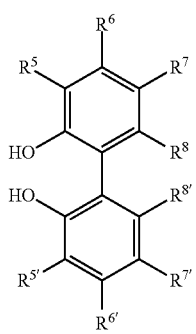

(3)

(in the formula (3), $R^5$, $R^6$, $R^7$, $R^5$, $R^{5'}$, $R^{6'}$, $R^{7'}$ and $R^{8'}$ independently represent a hydrogen atom, a hydroxyl group, a halogen atom, a saturated or unsaturated carbon chain, an optionally substituted aryl group, an optionally substituted heterocyclic group, an alkoxy group, an aryloxy group, an aralkyloxy group, a carboxyl group which may be protected by a protecting group, an amino group, a substituted amino group, a nitro group, an acyl group, a substituted silyl group or a polymer chain; and $R^5$ and $R^6$, $R^6$ and $R^7$, $R^7$ and $R^8$, $R^8$ and $R^{8'}$, $R^{8'}$ and $R^{7'}$, $R^{7'}$ and $R^{6'}$, or $R^{6'}$ and $R^{5'}$ may bind to each other to form a ring).

[6] The process according to the above [5], wherein the compound having, in a molecule, a formyl group and a double bond which allow carbonyl-ene cyclization is represented by the following general formula (4):

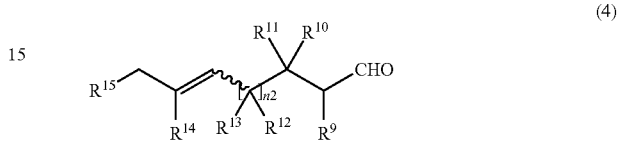

(4)

(in the formula (4), n2 represents an integer of 1 or 2; $R^9$, $R^{10}$ and $R^{12}$ independently represent a hydrogen atom or an optionally substituted alkyl group; $R^{11}$ represents an optionally substituted alkyl group or a hydroxyl group which may be protected by a protecting group; $R^{13}$, $R^{14}$ and $R^{15}$ independently represent a hydrogen atom or an optionally substituted alkyl group; and the wavy line represents configuration E or Z).

[7] The process according to the above [5], wherein the cyclized compound is represented by the following general formula (5):

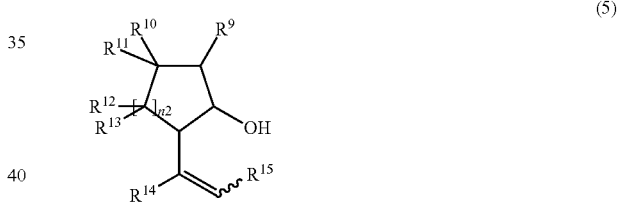

(5)

(in the formula (5), n2 represents an integer of 1 or 2; $R^9$, $R^{10}$ and $R^{12}$ independently represent a hydrogen atom or an optionally substituted alkyl group; $R^{11}$ represents an optionally substituted alkyl group or a hydroxyl group which may be protected by a protecting group; $R^{13}$, $R^{14}$ and $R^{15}$ independently represent a hydrogen atom or an optionally substituted alkyl group; and the wavy line represents configuration E or Z).

[8] The process according to the above [5], wherein the compound having, in a molecule, a formyl group and a double bond which allow carbonyl-ene cyclization is racemic citronellal or optically active citronellal, and the cyclized compound is optically active isopulegol.

[9] The process according to the above [8], wherein the optically active isopulegol is l-isopulegol.

[10] The process according to the above [8], wherein the optically active citronellal is l-citronellal.

Advantageous Effects of Invention

According to the present invention, cyclization of a compound having, in a molecule, a formyl group and a double bond which allow carbonyl-ene cyclization, the compound existing as a mixture of optical isomers thereof, increases the ratio of a particular optical isomer not only in a cyclized compound, but also in an unreacted compound, and thereby an objective optically active alcohol or olefin aldehyde can be obtained with a higher optical purity.

DESCRIPTION OF EMBODIMENTS

Figure 1:
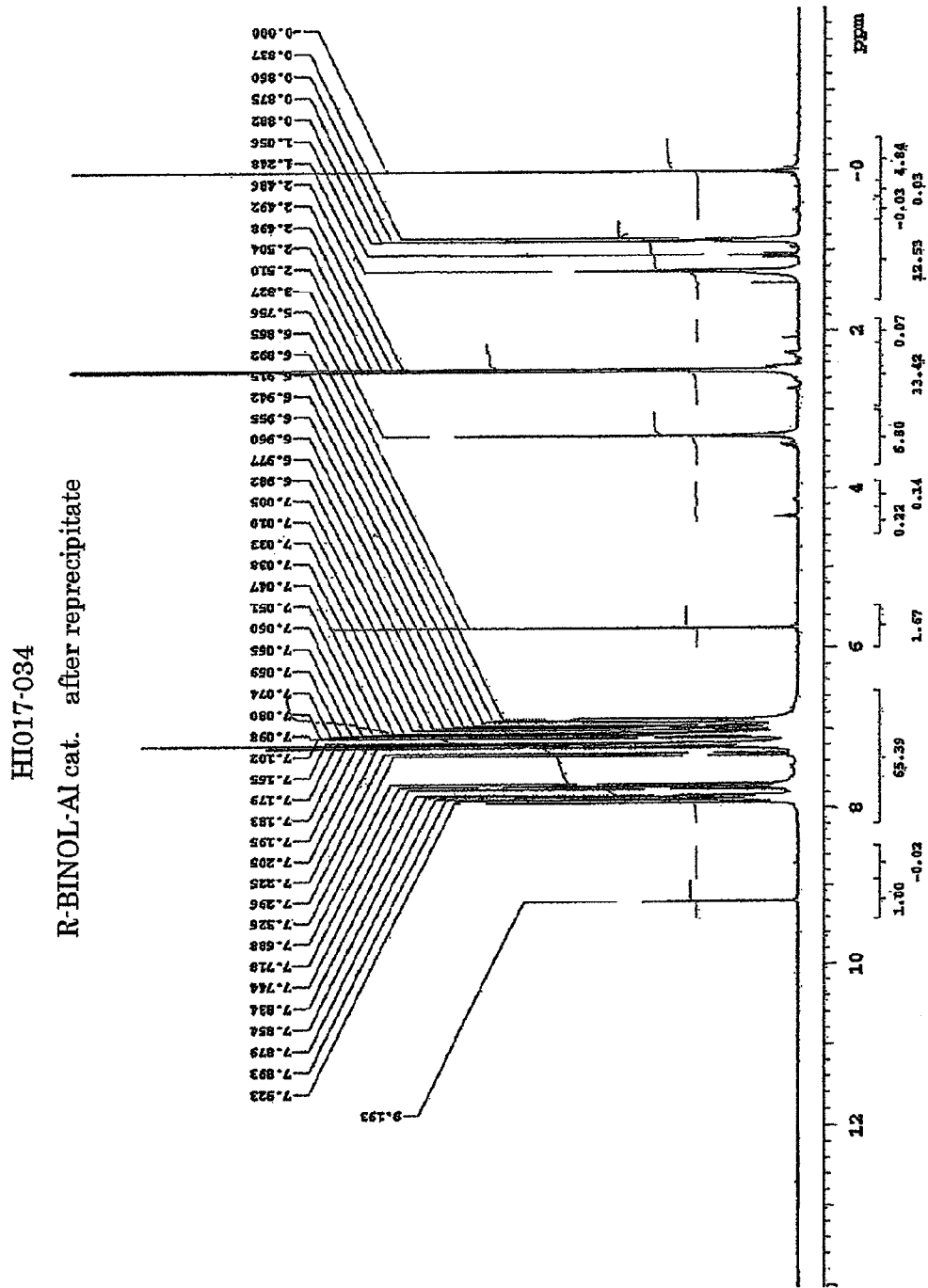
FIG. 1 shows the $^1$H-NMR chart of the solid product obtained in Example 1.

Hereinafter, the aluminum complex of the present invention will be described in more detail.

Regarding the aluminum compound (1) represented by the general formula (1) used for preparation of the aluminum complex of the present invention, Lg represents an alkyl group, an alkoxy group or a halogen atom.

The alkyl group represented by Lg refers to a straight or branched alkyl group having 1 to 8, preferably 1 to 4 carbon atoms, and preferable examples thereof include straight or branched alkyl groups having 1 to 4 carbon atoms, such as methyl, ethyl, propyl, isopropyl, n-butyl, sec-butyl, isobutyl and tert-butyl.

The alkoxy group represented by Lg refers to a straight or branched alkoxy group having 1 to 8, preferably 1 to 4 carbon atoms, and preferable examples thereof include straight or branched alkoxy groups having 1 to 4 carbon atoms, such as methoxy, ethoxy, propoxy, isopropoxy, n-butoxy, sec-butoxy, isobutoxy and tert-butoxy.

Examples of the halogen atom represented by Lg include a fluorine atom, a chlorine atom, a bromine atom and an iodine atom.

Regarding the biaryldiol compounds represented by the general formulae (2) and (3), and ligands derived from the biaryldiol compounds, which are represented by the general formulae (2') and (3'), $R^1$, $R^2$, $R^3$, $R^{1'}$, $R^{2'}$, $R^{3'}$, $R^5$, $R^6$, $R^7$, $R^8$, $R^{5'}$, $R^{6'}$, $R^{7'}$ and $R^{8'}$ independently represent a hydrogen atom, a halogen atom, a hydroxyl group, a saturated or unsaturated carbon chain, an optionally substituted aryl group, an optionally substituted heterocyclic group, an alkoxy group, an aryloxy group, an aralkyloxy group, a carboxyl group which may be protected by a protecting group, an amino group, a substituted amino group, a nitro group, an acyl group, a substituted silyl group or a polymer chain. $R^4$ and $R^{4'}$ independently represent a hydroxyl group, a halogen atom, a saturated or unsaturated carbon chain, an optionally substituted aryl group, an optionally substituted heterocyclic group, an alkoxy group, an aryloxy group, an aralkyloxy group, a carboxyl group which may be protected by a protecting group, an amino group, a substituted amino group, an acyl group, a substituted silyl group or a nitro group. $R^1$ and $R^2$, $R^2$ and $R^3$, $R^3$ and $R^4$, $R^4$ and $R^{4'}$, $R^{4'}$ and $R^{3'}$, $R^{3'}$ and $R^{2'}$, or $R^{2'}$ and $R^{1'}$ may bind to each other to form a ring. $R^5$ and $R^6$, $R^6$ and $R^7$, $R^7$ and $R^8$, $R^8$ and $R^{8'}$, $R^{8'}$ and $R^{7'}$, $R^{7'}$ and $R^{6'}$, or $R^{6'}$ and $R^{5'}$ may bind to each other to form a ring.

Regarding the biaryldiol compounds represented by the general formulae (2) and (3), groups represented by $R^1$, $R^2$, $R^3$, $R^4$, $R^{1'}$, $R^{2'}$, $R^{3'}$, $R^{4'}$, $R^5$, $R^6$, $R^7$, $R^8$, $R^{5'}$, $R^{6'}$, $R^{7'}$ or $R^{8'}$ will be described.

Examples of the saturated or unsaturated carbon chain include straight or branched alkyl groups having 1 to 6 carbon atoms, such as methyl, ethyl, propyl, isopropyl, n-butyl, sec-butyl, iso-butyl, tert-butyl, pentyl and hexyl; cyclic alkyl groups, such as cyclopentyl, cyclohexyl, methylcyclohexyl and cycloheptyl; and alkenyl or alkynyl groups, such as ethynyl, vinyl, styryl and allyl.

Examples of the halogen atom include a fluorine atom, a chlorine atom, a bromine atom and an iodine atom.

Examples of the optionally substituted aryl group include phenyl and naphthyl. Examples of the substituent in the aryl group include straight or branched alkyl groups having 1 to 4 carbon atoms, and straight or branched alkoxy groups having 1 to 4 carbon atoms.

Examples of the optionally substituted heterocyclic group include aliphatic heterocyclic groups, such as piperidino, piperazinyl, morpholino, tetrahydrofuryl, tetrahydropyranyl and tetrahydrothienyl; and aromatic heterocyclic groups, such as furyl, thienyl, pyridyl, pyrimidyl, pyrazyl, pyridazyl, pyrazolyl, imidazolyl, oxazolyl, thiazolyl, benzofuryl, benzothienyl, quinolyl, isoquinolyl, quinoxalyl, phthalazyl, quinazolyl, naphthyridyl, cinnolyl, benzimidazolyl, benzoxazolyl and benzothiazolyl.

Examples of the alkoxy group include methoxy, ethoxy, propoxy, isopropoxy, n-butoxy, tert-butoxy, pentyloxy, hexyloxy, heptyloxy and octyloxy.

Examples of the aryloxy group include phenoxy and naphthoxy. Examples of the aralkyloxy group include benzyloxy and 1-phenethyl.

Examples of the carboxyl group which may be protected by a protecting group include a carboxyl group; and alkoxycarbonyl groups having 2 to 5 carbon atoms, such as methoxycarbonyl.

Examples of the substituted amino group include mono- or di-alkylamino groups, such as N-methylamino, N,N-dimethylamino, N,N-diethylamino, N,N-diisopropylamino and N-cyclohexylamino; mono- or di-arylamino groups, such as N-phenylamino, N,N-diphenylamino, N,N-ditolylamino, N-naphthylamino and N-naphthyl-N-phenylamino; mono- or di-aralkylamino groups, such as N-benzylamino and N,N-dibenzylamino; and acylamino groups, such as acetylamino, benzoylamino and tert-butoxycarbonylamino.

Examples of the acyl group include aliphatic or aromatic acyl groups, such as acetyl, propionyl, butyryl, valeryl, pivaloyl, benzoyl, o-, m- or p-toluoyl, p-nitrobenzoyl and trifluoroacetyl.

Examples of the substituted silyl group include trimethylsilyl, triphenylsilyl, tri(p-tolyl)silyl and dimethylphenyl silyl.

Examples of the polymer chain include a 6,6-nylon chain, a vinyl polymer chain and a styrene polymer chain.

When n is 3 in the formula (1'), the aluminum complex of the present invention can be easily synthesized by a reaction of, in an inert organic solvent, the aluminum compound of the general formula (1) with the biaryldiol compound of the general formula (2), the molar ratio of which is 1.5- to 5-fold, and preferably 1.5- to 2-fold, relative to the aluminum compound. The reaction temperature ranges, for example, −30 to 60° C., preferably −10 to 40° C., and more preferably 0 to 30° C. The reaction duration is, for example, 0.25 to 30 hours, and preferably 0.5 to 2 hours. Examples of the inert organic solvent include hydrocarbons (hexane, heptane, benzene, toluene, xylene, etc.), ethers (diethyl ether, diisopropyl ether, tetrahydrofuran, etc.) and halogenated hydrocarbons (dichloromethane, dichloroethane, chlorobenzene, bromotoluene, etc.). The aluminum compound (1), and the biaryldiol compound represented by the general formula (2) may be used in the form of a solution diluted with the inert organic solvent, and one of the solutions may be added all at once or dropwise slowly to the other.

When n is 2, the aluminum complex of the present invention can be easily synthesized as follows. First, the aluminum compound of the formula (1) is allowed to react with the biaryldiol compound of the formula (2), the molar ratio of which is 1.1- to 1.3-fold relative to the aluminum compound, in the same inert organic solvent as exemplified in the case where n is 3. The reaction temperature ranges, for example, -30 to 60° C., preferably -10 to 40° C., and more preferably 0 to 30° C. The reaction duration is, for example, 0.25 to 30 hours, and preferably 0.5 to 2 hours. Next, 0.4 Eq or more of the biaryldiol compound of the formula (3) is added to the reaction mixture of the aluminum compound of the formula (1) and the diol compound of the formula (2), which is obtained in the above reaction, and then a further reaction is allowed to proceed. The reaction temperature ranges, for example, -30 to 60° C., preferably -10 to 40° C., and more preferably 0 to 30° C. The reaction duration is, for example, 0.25 to 30 hours, and preferably 0.5 to 2 hours. The biaryldiol compound of the formula (3) may be diluted with the solvent or not diluted before added to the reaction mixture. Also, the biaryldiol compound of the formula (3) may be added thereto all at once or dropwise slowly. The biaryldiol compound of the formula (3) can be added to the reaction mixture of the aluminum compound of the formula (1) and the biaryldiol compound of the formula (2), and vice versa. It is preferable to ensure that the biaryldiol compound of the formula (2) and the biaryldiol compound of the formula (3) separately react with the aluminum compound (1). It is preferable to avoid simultaneous addition of both biaryldiol compounds.

Preferable examples of the biaryldiol compound represented by the formula (2) or (3) of the present invention include, but are not limited to, the following compounds.

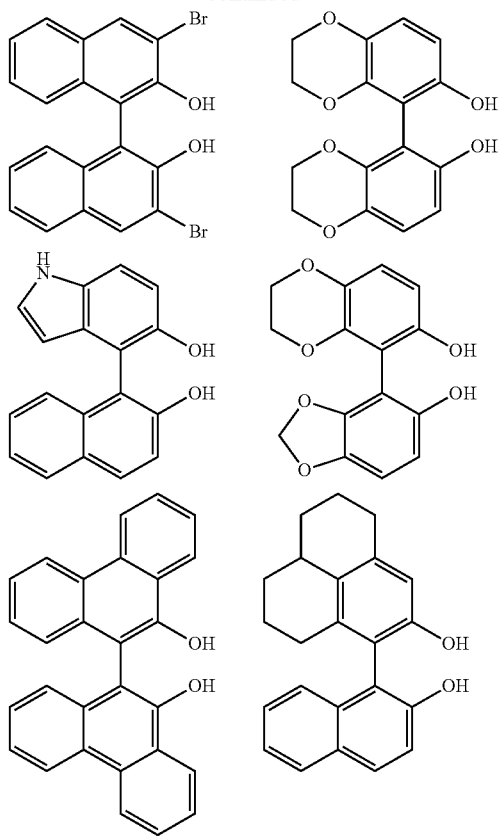

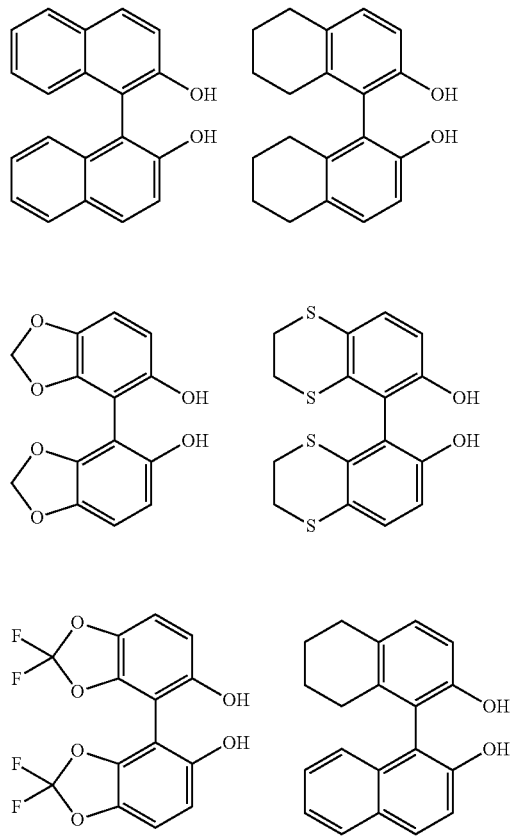

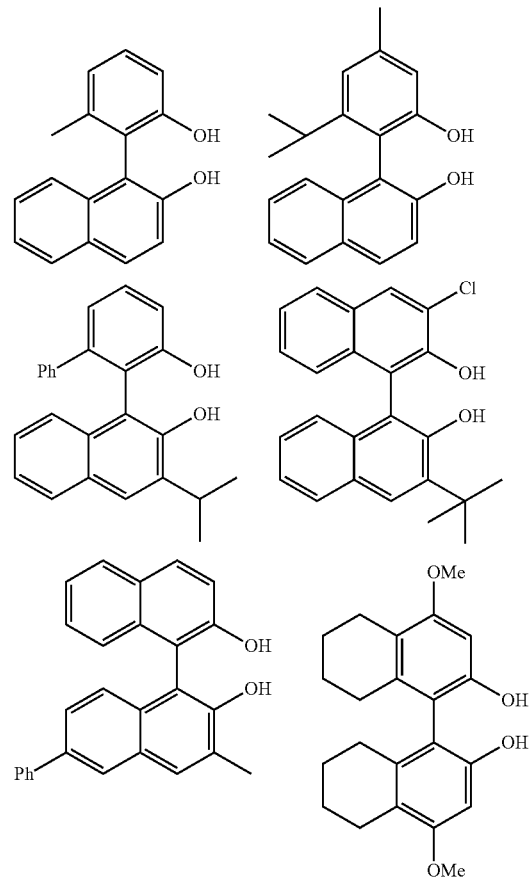

-continued
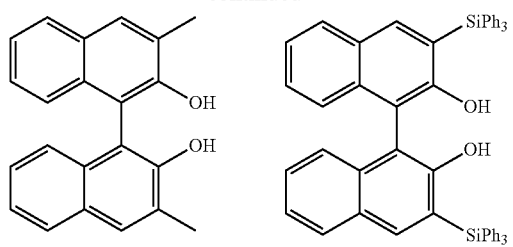
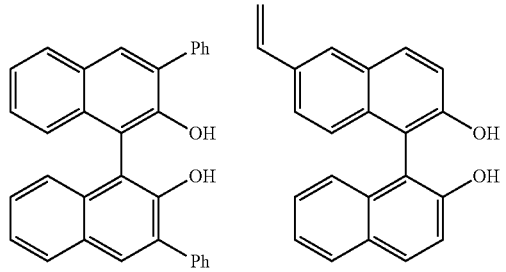
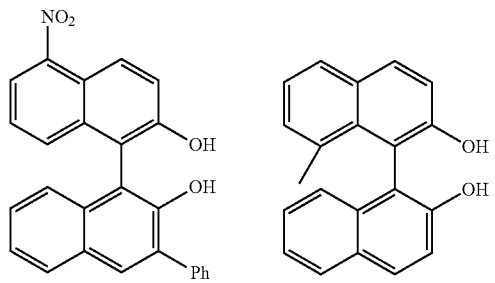
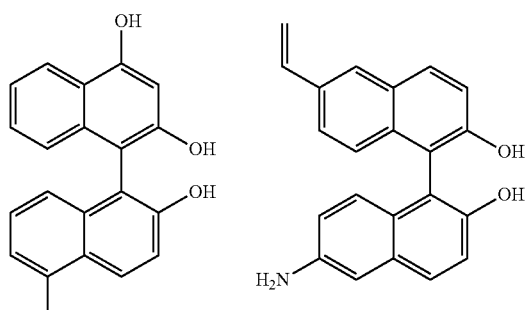
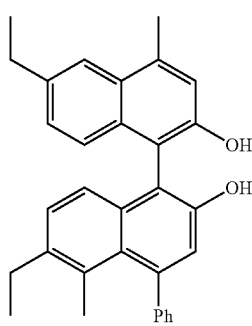
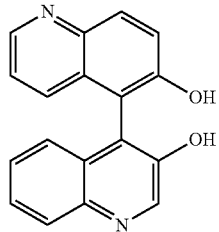
-continued
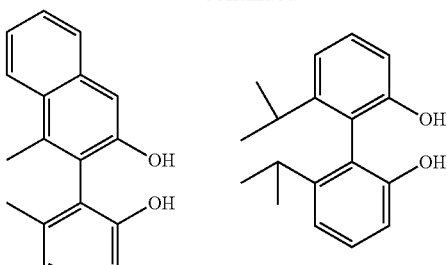
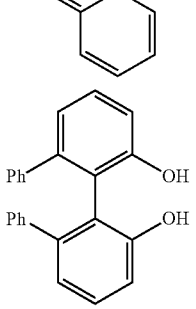
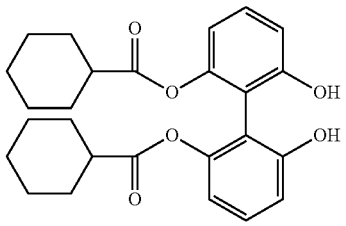
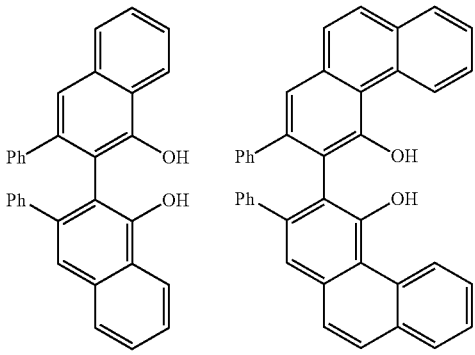
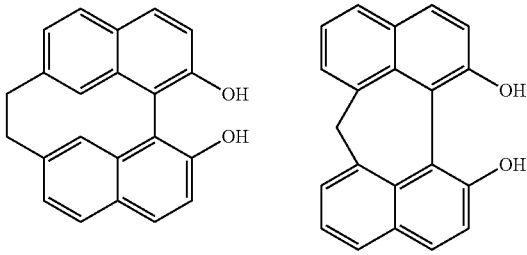
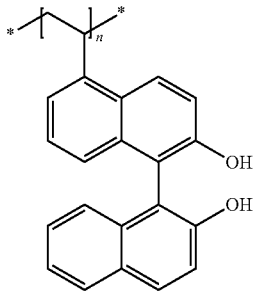

-continued
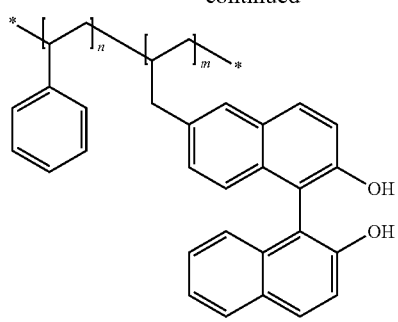
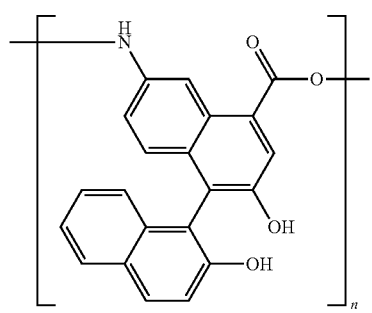
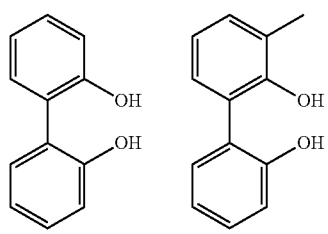
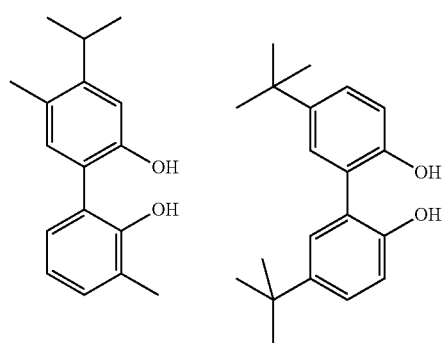
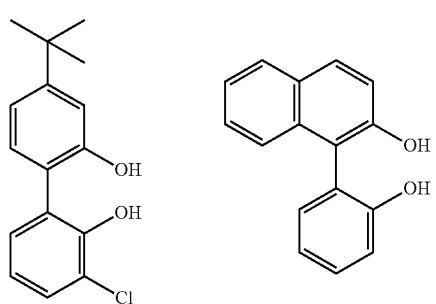
-continued
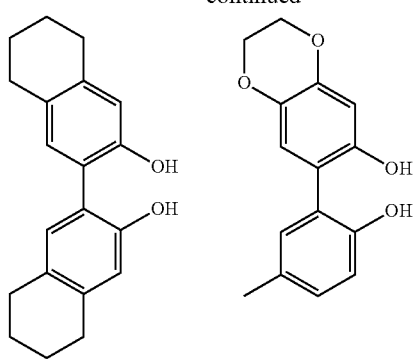
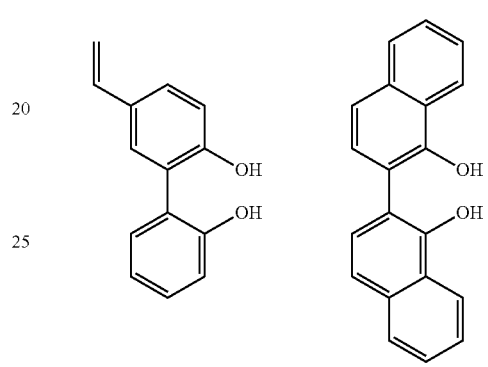
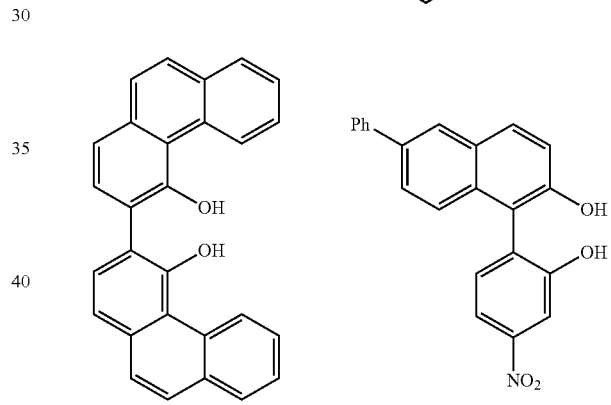
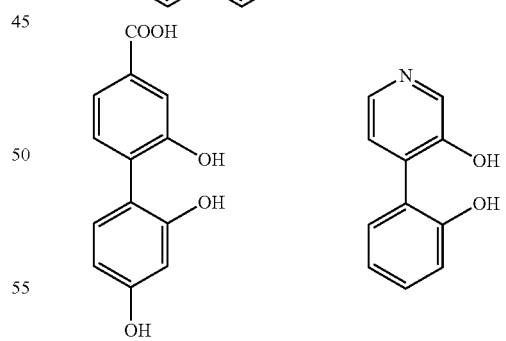
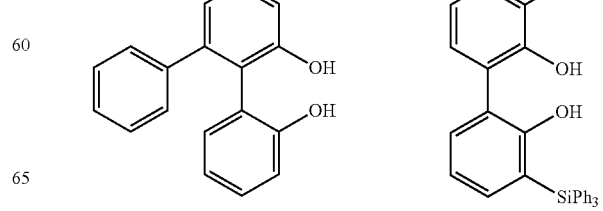

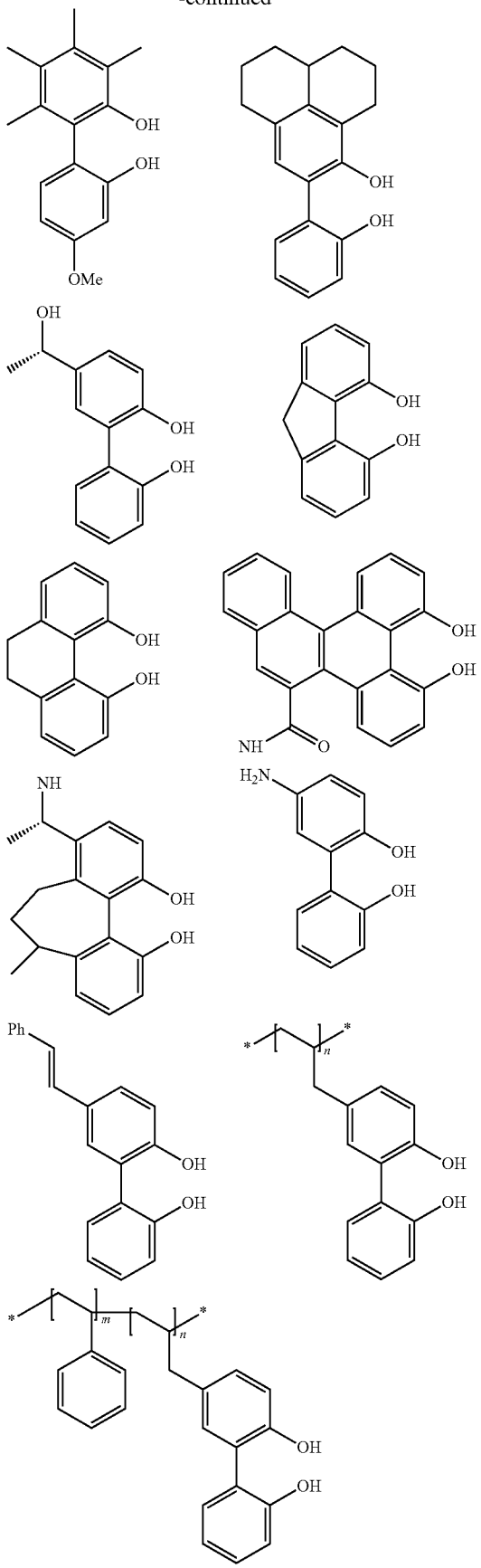

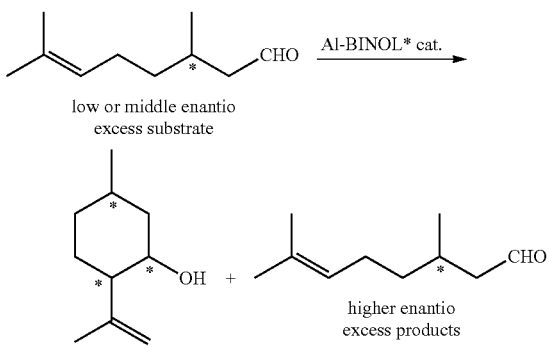

Next, the compounds represented by the general formulae (4) and (5) used for selective cyclization of the present invention will be described.

Regarding the compounds represented by the general formulae (4) and (5), the optionally substituted alkyl group represented by $R^9$, $R^{10}$, $R^{11}$, $R^{12}$, $R^{13}$, $R^{14}$ or $R^{15}$ refers to a straight or branched alkyl group having 1 to 8, preferably 1 to 4 carbon atoms, and preferable examples thereof include alkyl groups having 1 to 4 carbon atoms, such as methyl, ethyl, propyl, isopropyl, n-butyl, sec-butyl, isobutyl and tert-butyl.

Examples of the substituent in the alkyl group include alkoxy groups having 1 to 6 carbon atoms, such as methoxy and ethoxy; and aryl groups, such as phenyl, naphthyl and tolyl.

Regarding the hydroxyl group which may be protected by a protecting group, which is represented by $R^{11}$, examples of the protecting group include acyl groups, such as acetyl, benzoyl and methoxycarbonyl; aralkyl groups, such as benzyl; and substituted silyl groups, such as trimethylsilyl and t-butyldimethylsilyl.

Subsequently, the preparation process of the present invention, i.e., the selective cyclization which increases the ratio of a particular optical isomer, will be described below by citing, as an example, production of isopulegol via cyclization of citronellal using an aluminum complex having 1,1'-bi-2-naphthol (BINOL) as a biaryldiol compound.

However, the example below is intended for illustrative purpose only, and the present invention is not limited to the substrate and product shown below.

(In the scheme, * represents a chiral carbon.)

Namely, citronellal having a low to middle optical purity is subjected to enantioselective cyclization using the aluminum-optically active binaphthol complex of the present invention as a catalyst, and thereby isopulegol and citronellal can be obtained with a higher optical purity than that of the substrate citronellal.

The amount of the aluminum complex used for the cyclization of the present invention is not particularly limited, but it is usually 0.05 to 10 mol %, preferably 0.5 to 5 mol %, and more preferably 0.7 to 2 mol % relative to that of citronellal in terms of moles of aluminum.

The preparation method of the aluminum complex used for the cyclization of the present invention is as follows, for example.

(a) (i) mixing 1 Eq of the aluminum compound of the formula (1) with 1.0 Eq or more of the optically active biaryldiol compound having a chiral axis represented by the formula (2) in a reaction system, to prepare a complex, or (ii) allowing 1 Eq of the aluminum compound of the formula (1) to react with 1.0 to 1.3 Eq of the optically active biaryldiol compound having a chiral axis represented by the formula (2), and mixing therewith 0.4 to 1.0 Eq of the optically active biaryldiol compound having a chiral axis or racemic biaryldiol compound represented by the formula (3), to prepare a complex, and then adding thereto citronellal (the in situ method).

(b) mixing citronellal and a complex isolated after the above-mentioned preparation at the time of cyclization. Usually, each method of (a) and (b) produces the same results.

The temperature of the cyclization is not particularly limited, but it is usually −30 to 50° C., preferably −10 to 30° C., and more preferably 0 to 20° C. The reaction is allowed to proceed with the temperature kept within the above-mentioned ranges for usually 0.25 to 30 hours, and preferably 0.5 to 20 hours, and thereby gives isopulegol easily.

The cyclization of the present invention may be performed without any solvent or in the presence of an inert solvent. Any solvent can be used without particular limitation as long as it does not significantly disturb the cyclization, and examples thereof include aliphatic hydrocarbons, such as hexane, heptane and octane; alicyclic hydrocarbons, such as cyclohexane and methylcyclohexane; aromatic hydrocarbons, such as benzene, toluene and xylene; halogenated hydrocarbons, such as dichloromethane, dichloroethane, chlorobenzene and bromotoluene; and ethers, such as diethyl ether, diisopropyl ether, dimethoxyethane, tetrahydrofuran, dioxane and dioxolane. Inter alia, aliphatic or aromatic hydrocarbons, such as toluene and heptane, are more preferred.

The amount of the solvent ranges usually O— to 20-fold, and preferably 0.5- to 7-fold relative to that of citronellal. The cyclization is preferably performed in an inert gas (such as nitrogen or argon gas) atmosphere for smooth progress of cyclization.

After completion of the cyclization, ordinary post-treatment, such as distillation, crystallization and various kinds of chromatography, may be performed alone or in combination thereof, for purification of the resulting product. For example, in the case of purification of isopulegol, highly purified isopulegol can be obtained simply by distillation, without need of low temperature separation. After distillation, the residue may be subjected to ordinary treatment with an acid or an alkali for removal of impurities etc. including aluminum, and subsequent crystallization. Thus, ligands can be recovered.

EXAMPLES

Hereinafter, the present invention will be illustrated in detail by Comparative Examples and Examples, but the present invention is not limited thereto.

Measurement of the product was performed by gas chromatography (GC). The conditions used for the measurement are as follows.
Analytical instrument: G5000 (Hitachi)
Column:
  Conversion rate measurement BC-WAX (0.25 mm×30 m) (GL Sciences)
  Optical purity measurement β-DEX 225 (0.25 mm×30 m) (SPELCO), β-DEX 325 (0.25 mm×30 m) (SPELCO)
Detector: FID
The optical purity of each citronellal used in Examples is as follows.
d-citronellal: 97.8% e.e.
l-citronellal: 96.6% e.e.
Racemic citronellal: 0.74% e.e.

Example 1

Aluminum Complex Preparation and L-Isopulegol Synthesis

In a 200-ml reaction flask, 1.31 g (4.59 mmol) of (R)-1,1'-bi-2-naphthol was placed and the air in the flask was replaced with nitrogen gas. Then, 46 ml of methylene chloride and 3 ml (3 mmol) of a hexane solution of triethylaluminum (1.0 mol/L) were successively added thereto and the mixture was stirred at room temperature for 1 hour. After this, the solvent was distilled off and 1.40 g of a colorless to light orange solid was obtained. The solid was reprecipitated with methylene chloride/hexane, and the resulting product was analyzed by $^1$H-NMR. The analysis results are as follows.

$^1$H-NMR (DMSO-$d_6$): 6.86-7.26 (m, 24H), 7.68-7.93 (m, 12H)

Figure 2:
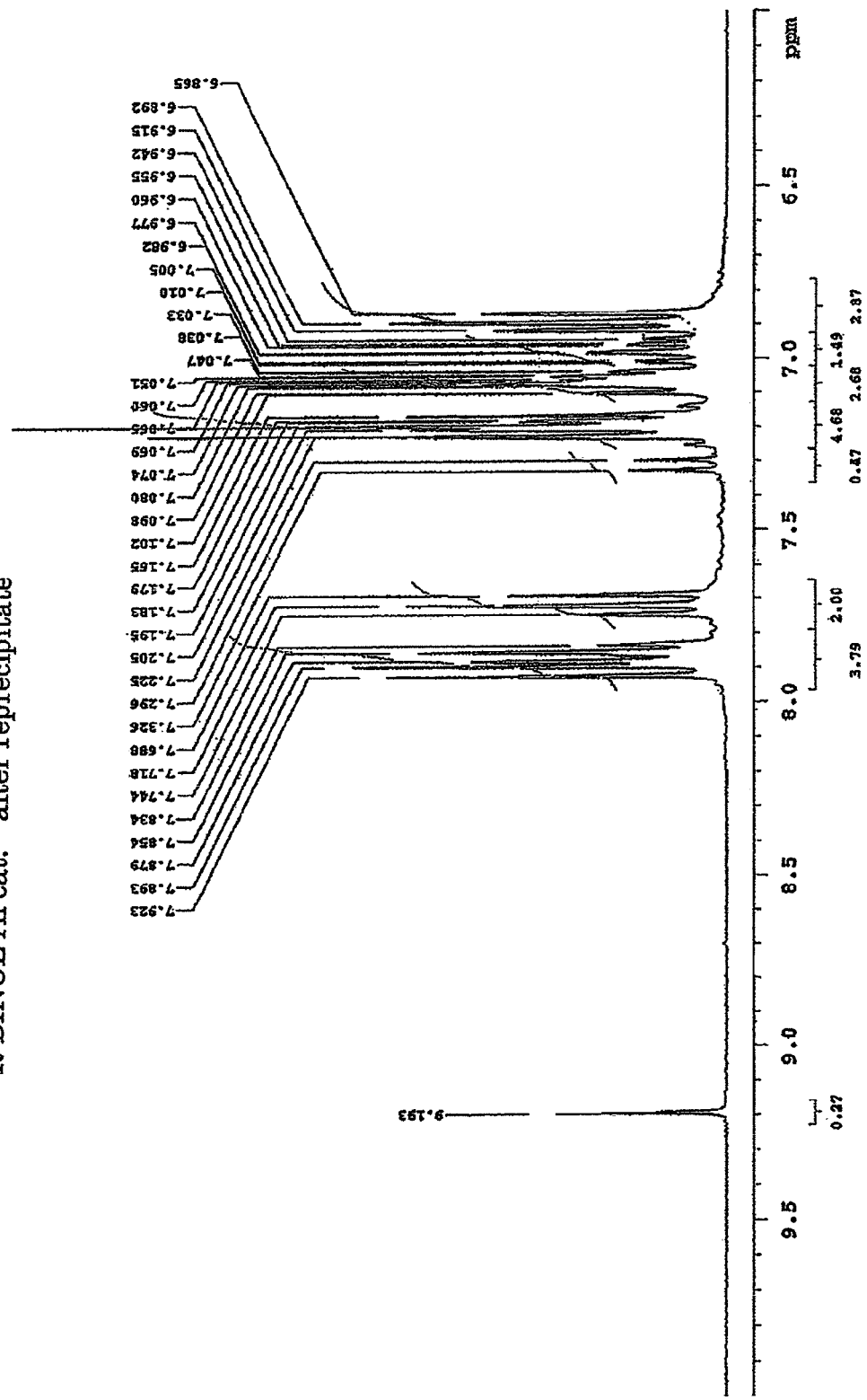
FIG. 2 shows the enlarged view of the lower field in the $^1$H-NMR chart of FIG. 1.

The NMR chart is shown in FIG. 1, and the enlarged view of the lower field thereof is shown in FIG. 2.

270 mg of the solid obtained above was added to 1.54 g (10 mmol) of d-citronellal cooled to a temperature of 0 to 5° C., and the mixture was stirred at a temperature of 0 to 5° C. for 1 hour. After completion of the reaction, 2 ml of water and 2 ml of toluene were added thereto, and the organic layer was analyzed by GC. According to the analysis results, the substrate conversion rate was 81.1%, the l-isopulegol selectivity was 94.0%, and the ratio of l-isopulegol to the other isomers was 96.1:3.9.

Example 2

L-Isopulegol Synthesis

In a 50-ml Schlenk flask, 229 mg (0.8 mmol) of (R)-1,1'-bi-2-naphthol was placed and the air in the flask was replaced with nitrogen gas. Then, 4.6 ml of toluene and 0.5 ml (0.5 mmol) of a toluene solution of triethylaluminum (1.0 mol/L) were successively added thereto and the mixture was stirred at room temperature for 1 hour, to give a catalyst solution. After the catalyst solution was cooled to a temperature of 0 to 5° C., 1.54 g (10 mmol) of d-citronellal was added dropwise thereto, and the mixture was stirred at a temperature of 0 to 5° C. for 1 hour. After completion of the reaction, 2 ml of water was added thereto, and the organic layer was analyzed by GC. According to the analysis results, the substrate conversion rate was 98.5%, the l-isopulegol selectivity was 93.8%, and the ratio of l-isopulegol to the other isomers was 98.3:1.7.

Example 3

L-Isopulegol Synthesis

The same experiment as described in Example 2 was performed except that 229 mg of (S)-2,2'-dihydroxy-1,1'-binaphthyl was used instead of (R)-1,1'-bi-2-naphthol in Example 2. According to the analysis results, the substrate conversion rate was 37.4%, the l-isopulegol selectivity was 100%, and the ratio of l-isopulegol to the other isomers was 73.6:26.4.

Example 4

L-Isopulegol Synthesis

In a 50-ml Schlenk flask, 22.9 mg (0.08 mmol) of (R)-1,1'-bi-2-naphthol was placed and the air in the flask was replaced with nitrogen gas. Then, 4.6 ml of toluene and 0.05 ml (0.05 mmol) of a toluene solution of triethylaluminum (1.0 mol/L) were successively added thereto and the mixture was stirred at room temperature for 1 hour, to give a catalyst solution. After the catalyst solution was cooled to a temperature of 0 to 5° C., 1.54 g (10 mmol) of d-citronellal was added dropwise thereto, and the mixture was stirred at a temperature of 0 to 5° C. for 20 hours. After completion of the reaction, 2 ml of water was added thereto, and the organic layer was analyzed by GC. According to the analysis results, the substrate conversion rate was 94.9%, the l-isopulegol selectivity was 92.5%, and the ratio of l-isopulegol to the other isomers was 97.0:3.0.

Example 5

L-Isopulegol Synthesis

In a 50-ml Schlenk flask, 229 mg (0.8 mmol) of (R)-1,1'-bi-2-naphthol was placed and the air in the flask was replaced with nitrogen gas. Then, 4.6 ml of methylene chloride and 0.5 ml (0.5 mmol) of a toluene solution of triethylaluminum (1.0 mol/L) were successively added thereto and the mixture was stirred at room temperature for 1 hour, to give a catalyst solution. The catalyst solution was concentrated in vacuo for solidification, and then a white to light yellow solid was obtained. In a nitrogen atmosphere, the solid was quickly added to a mixed solution of 1.54 g (10 mmol) of d-citronellal and 4.6 ml of toluene, which was previously cooled to a temperature of 0 to 5° C., and the mixture was stirred at a temperature of 0 to 5° C. for 1 hour. After completion of the reaction, 2 ml of water was added thereto, and the organic layer was analyzed by GC. According to the analysis results, the substrate conversion rate was 94.4%, the l-isopulegol selectivity was 93.0%, and the ratio of l-isopulegol to the other isomers was 96.9:3.1.

Example 6

D-Isopulegol Synthesis

In a 50-ml Schlenk flask, 229 mg (0.8 mmol) of (S)-1,1'-bi-2-naphthol was placed and the air in the flask was replaced with nitrogen gas. Then, 4.6 ml of toluene and 0.5 ml (0.5 mmol) of a toluene solution of triethylaluminum (1.0 mol/L) were successively added thereto and the mixture was stirred at room temperature for 1 hour, to give a catalyst solution. After the catalyst solution was cooled to a temperature of 0 to 5° C., 1.54 g (10 mmol) of l-citronellal was added dropwise thereto, and the mixture was stirred at a temperature of 0 to 5° C. for 1 hour. After completion of the reaction, 2 ml of water was added thereto, and the organic layer was analyzed by GC. According to the analysis results, the substrate conversion rate was 94.8%, the d-isopulegol selectivity was 95.7%, and the ratio of d-isopulegol to the other isomers was 97.2:2.8.

Example 7

D-Isopulegol Synthesis

The same experiment as described in Example 6 was performed except that 229 mg of (R)-2,2'-dihydroxy-1,1'-binaphthyl was used instead of (S)-1,1'-bi-2-naphthol in Example 6. According to the analysis results, the substrate conversion rate was 51.2%, the d-isopulegol selectivity was 84.9%, and the ratio of d-isopulegol to the other isomers was 62.9:37.1.

Example 8

Synthesis of L-Isopulegol from Racemic Citronellal

In a 50-ml Schlenk flask, 258 mg (0.9 mmol) of (R)-1,1'-bi-2-naphthol was placed and the air in the flask was replaced with nitrogen gas. Then, 5.8 ml of methylene chloride, 5.8 ml of toluene and 0.5 ml (0.5 mmol) of a toluene solution of triethylaluminum (1.0 mol/L) were successively added thereto and the mixture was stirred at room temperature for 1 hour, to give a catalyst solution. After the catalyst solution was cooled to a temperature of 0 to 5° C., 3.86 g (25 mmol) of racemic citronellal was added dropwise thereto, and the mixture was stirred at a temperature of 0 to 5° C. for 1 hour. After completion of the reaction, 2 ml of water was added thereto, and the organic layer was analyzed by GC. According to the analysis results, the substrate conversion rate was 48.9%, the isopulegol selectivity was 95.6%, the enantioselectivity for l-citronellal was 53.6% e.e., and the enantioselectivity for l-n-isopulegol was 67.7% e.e.

Example 9

L-Isopulegol Synthesis

In a 300-ml reaction flask, 2.29 g (8.0 mmol) of (R)-1,1'-bi-2-naphthol was placed and the air in the flask was replaced with nitrogen gas. Then, 116 ml of toluene and 5 ml (5.0 mmol) of a toluene solution of triethylaluminum (1.0 mol/L) were successively added thereto and the mixture was stirred at room temperature for 1 hour, to give a catalyst solution. After the catalyst solution was cooled to a temperature of 0 to 5° C., 38.6 g (250 mmol) of d-citronellal was slowly added dropwise thereto, and the mixture was stirred at a temperature of 0 to 5° C. for 9 hours. After completion of the reaction, the reaction mixture was concentrated in vacuo, and continuously toluene was distilled off at a temperature of 110 to 115° C. at a pressure of 2.93 to 3.33 kPa (22 to 25 mmHg), to give 31.0 g of the objective l-isopulegol at the yield of 80.3%. The GC analysis results show that the purity was 99.0% and that the ratio of l-isopulegol to the other isomers was 98.7:1.3.

The residue obtained after distillation was diluted with toluene, washed with an aqueous sulfuric acid solution, concentrated and subjected to crystallization with a toluene/heptane solution, and then 1.65 g of (R)-1,1'-bi-2-naphthol was recovered. Using the recovered BINOL, the same reaction as described in Example 1 was performed. According to the analysis results, the substrate conversion rate was 95.1%, the l-isopulegol selectivity was 99.2%, and the ratio of l-isopulegol to the other isomers was 97.5:2.5.

Example 10

Synthesis of L-Isopulegol from Citronellal Having an Excess of D-Isomer

In a 50-ml Schlenk flask, 258 mg (0.9 mmol) of (R)-1,1'-bi-2-naphthol was placed and the air in the flask was replaced with nitrogen gas. Then, 5.8 ml of methylene chloride, 5.8 ml of toluene and 0.5 ml (0.5 mmol) of a toluene solution of triethylaluminum (1.0 mol/L) were successively added thereto and the mixture was stirred at room temperature for 1 hour, to give a catalyst solution. After the catalyst solution was cooled to a temperature of 0 to 5° C., 3.86 g (25 mmol) of 60% ee citronellal (having an excess of d-isomer) was added dropwise thereto, and the mixture was stirred at a temperature of 0 to 5° C. for 3 hours. After completion of the reaction, 2 ml of water was added thereto, and the organic layer was analyzed by GC. According to the analysis results, the substrate conversion rate was 71.1%, the isopulegol selectivity was 99.6%, the enantioselectivity for l-citronellal was 8.90% e.e., and the enantioselectivity for l-n-isopulegol was 91.0% e.e.

Example 11

Synthesis of L-Isopulegol from Citronellal Having an Excess of D-Isomer

In a 50-ml Schlenk flask, 258 mg (0.9 mmol) of (R)-1,1'-bi-2-naphthol was placed and the air in the flask was replaced with nitrogen gas. Then, 5.8 ml of methylene chloride, 5.8 ml of toluene and 0.5 ml (0.5 mmol) of a toluene solution of triethylaluminum (1.0 mol/L) were successively added thereto and the mixture was stirred at room temperature for 1 hour, to give a catalyst solution. After the catalyst solution was cooled to a temperature of 0 to 5° C., 3.86 g (25 mmol) of 20% ee citronellal (having an excess of d-isomer) was added dropwise thereto, and the mixture was stirred at a temperature of 0 to 5° C. for 2 hours. After completion of the reaction, 2 ml of water was added thereto, and the organic layer was analyzed by GC. According to the analysis results, the substrate conversion rate was 61.7%, the isopulegol selectivity was 99.5%, the enantioselectivity for l-citronellal was 60.8% e.e., and the enantioselectivity for l-n-isopulegol was 76.4% e.e.

Example 12

Improvement of Optical Purity of Citronellal Having an Excess of D-Isomer

In a 50-ml Schlenk flask, 258 mg (0.9 mmol) of (S)-1,1'-bi-2-naphthol was placed and the air in the flask was replaced with nitrogen gas. Then, 5.8 ml of methylene chloride, 5.8 ml of toluene and 0.5 ml (0.5 mmol) of a toluene solution of triethylaluminum (1.0 mol/L) were successively added thereto and the mixture was stirred at room temperature for 1 hour, to give a catalyst solution. After the catalyst solution was cooled to a temperature of 0 to 5° C., 3.86 g (25 mmol) of 60% ee citronellal (having an excess of d-isomer) was added dropwise thereto, and the mixture was stirred at a temperature of 0 to 5° C. for 3 hours. After completion of the reaction, 2 ml of water was added thereto, and the organic layer was analyzed by GC. According to the analysis results, the substrate conversion rate was 29.4%, the isopulegol selectivity was 98.9%, the enantioselectivity for d-citronellal was 84.3% e.e., and the enantioselectivity for d-n-isopulegol was 23.7% e.e.

Examples 13 to 20

Synthesis of L-Isopulegol Using Aluminum Catalyst

The results of synthesis using various biaryldiols are shown below. The reaction conditions are as follows. In a 50-ml Schlenk flask, a given Eq of the biaryldiol compound of the general formula (2) ($L^1H_2$) was placed and the air in the flask was replaced with nitrogen gas. Then, 4.6 ml of a given solvent and triethylaluminum (0.5 mmol) were successively added thereto and the mixture was stirred at room temperature for 1 hour, to give a catalyst solution. Alternatively, a given Eq of the biaryldiol compound of the general formula (3) ($L^2H_2$) was further added to the reaction mixture and the mixture was stirred at room temperature for 1 hour, to give a catalyst solution. After the catalyst solution was cooled to a temperature of 0 to 5° C., 1.54 g (10 mmol) of citronellal was added dropwise thereto, and the mixture was stirred at a temperature of 0 to 5° C. for 1 hour. After completion of the reaction, 2 ml of water was added thereto, and the organic layer was analyzed by GC.

In the table, conv. represents the conversion rate of citronellal, sel. represents the selectivity for isopulegol, and n-sel. represents the selectivity for n-isopulegol. (R)-BINOL, (R)—H8-BINOL, BIPOL and (R)-DiBr—H8-BINOL represent the following compounds.

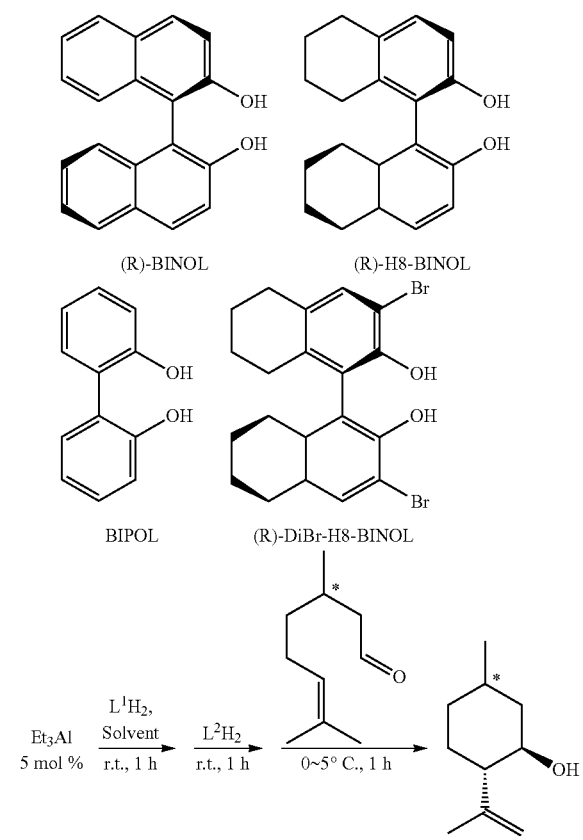

(In the scheme, Et represents an ethyl group, $L^1H_2$ represents a biaryldiol compound represented by the general formula (2), $L^2H_2$ represents a biaryldiol compound represented by the general formula (3), and * represents a chiral carbon.)

TABLE 1

| Ex. | Solvent | L¹H₂ (eq vs Et₃Al) | L²H₂ (eq vs Et₃Al) | Conv. (%) | Sel. (%) | n-sel. (%) |
|-----|---------|---------------------|---------------------|-----------|----------|------------|
| 13 | CH₂Cl₂ | (R)-BINOL (1 eq) | BIPOL (0.6 eq) | 96.9 | 99.7 | 97.9 |
| 14 | CH₂Cl₂ | (R)-BINOL (1 eq) | BIPOL (0.6 eq) | 45.7 | 100 | 66.0 |
| 15 | CH₂Cl₂ | BIPOL (1 eq) | (R)-BINOL (0.6 eq) | 15.4 | 100 | 75.9 |
| 16 | Toluene | (R)-BINOL 1 eq | (R)—H8-BINOL 0.6 eq | 64.7 | 73.8 | 95.9 |
| 17 | Toluene | (R)—H8-BINOL 1 eq | (R)-BINOL 0.6 eq | 54.6 | 85.1 | 95.8 |
| 18 | Toluene | (R)-BINOL 2.5 eq | — | 98.3 | 100 | 98.3 |
| 19 | Toluene | (R)-BINOL 5 eq | — | 96.9 | 100 | 95.1 |
| 20 | CH₂Cl₂ | (R)-DiBr—H8-BINOL 1.5 eq | — | 90.5 | 99.2 | 94.7 |

The substrate used in Example 14 was l-citronellal, and the substrate used in the other Examples in the table was d-citronellal.

Example 21

Synthesis of L-Isopulegol from Racemic Citronellal

In a 50-ml Schlenk flask, 129 mg (0.45 mmol) of (R)-1,1'-bi-2-naphthol was placed and the air in the flask was replaced with nitrogen gas. Then, 2 ml of methylene chloride, 2 ml of toluene and 0.18 ml (0.25 mmol) of a hexane solution of trimethylaluminum (1.4 mol/L) were successively added thereto and the mixture was stirred at room temperature for 7 hours, to give a catalyst solution. After the catalyst solution was cooled to a temperature of 0 to 5° C., 1.93 g (12.5 mmol) of racemic citronellal was added dropwise thereto, and the mixture was stirred at a temperature of 0 to 5° C. for 1 hour. After completion of the reaction, 2 ml of water was added thereto, and the organic layer was analyzed by GC. According to the analysis results, the substrate conversion rate was 46.5%, the isopulegol selectivity was 87.6%, the enantioselectivity for l-citronellal was 43.8% e.e., and the enantioselectivity for l-n-isopulegol was 76.0% e.e.

Example 22

Synthesis of L-Isopulegol from Racemic Citronellal

In a 50-ml Schlenk flask, 178 mg (0.4 mmol) of (R)-3,3'-dibromo-1,1'-bi-2-naphthol was placed and the air in the flask was replaced with nitrogen gas. Then, 9 ml of methylene chloride and 0.4 ml (0.4 mmol) of a toluene solution of triethylaluminum (1.0 mol/L) were successively added thereto and the mixture was stirred at room temperature for 1 hour, to give a catalyst solution. After the catalyst solution was cooled to a temperature of 0 to 5° C., 3.09 g (20 mmol) of racemic citronellal was added dropwise thereto, and the mixture was stirred at a temperature of 0 to 5° C. for 5 hours. After completion of the reaction, 2 ml of water was added thereto, and the organic layer was analyzed by GC. According to the analysis results, the substrate conversion rate was 50.5%, the isopulegol selectivity was 61.6%, the enantioselectivity for l-citronellal was 15.6% e.e., and the enantioselectivity for l-n-isopulegol was 26.3% e.e.

In the case where 285 mg (0.64 mmol) of (R)-3,3'-dibromo-1,1'-bi-2-naphthol was used and 9-hour stirring for cyclization was performed, the substrate conversion rate was 42.8%, the isopulegol selectivity was 92.7%, the enantioselectivity for l-citronellal was 23.3% e.e., and the enantioselectivity for l-n-isopulegol was 42.6% e.e.

Example 23

Synthesis of D-Isopulegol from Racemic Citronellal

In a 50-ml Schlenk flask, 214 mg (0.3 mmol) of (R)-3,3'-bis(triphenylsilyl)-1,1'-bi-2-naphthol was placed and the air in the flask was replaced with nitrogen gas. Then, 7 ml of toluene and 0.3 ml (0.3 mmol) of a toluene solution of triethylaluminum (1.0 mol/L) were successively added thereto and the mixture was stirred at room temperature for 1 hour, to give a catalyst solution. After the catalyst solution was cooled to a temperature of 0 to 5° C., 2.31 g (15 mmol) of racemic citronellal was added dropwise thereto, and the mixture was stirred at a temperature of 0 to 5° C. for 1 hour. After completion of the reaction, 2 ml of water was added thereto, and the organic layer was analyzed by GC. According to the analysis results, the substrate conversion rate was 55.3%, the isopulegol selectivity was 71.9%, the enantioselectivity for d-citronellal was 7.20% e.e., and the enantioselectivity for d-n-isopulegol was 14.6% e.e.

In the case where 386 mg (0.48 mmol) of (R)-3,3'-bis(triphenylsilyl)-1,1'-bi-2-naphthol was used and 1-hour stirring for cyclization was performed, the substrate conversion rate was 55.0%, the isopulegol selectivity was 70.3%, the enantioselectivity for d-citronellal was 6.43% e.e., and the enantioselectivity for d-n-isopulegol was 17.0% e.e.

Comparative Examples 1 to 4

Isopulegol Production by Cyclization of Citronellal Using Lithium Aluminum Hydride as Aluminum Compound In a 50-ml Schlenk flask, 229 mg (0.8 mmol, 1.6 eq) or 300 mg (1.05 mmol, 2.1 eq) of (R)-1,1'-bi-2-naphthol was placed and the air in the flask was replaced with nitrogen gas. Then, 4.6 ml of a given solvent and 19 mg (0.5 mmol) of lithium aluminum hydride were successively added thereto and the mixture was stirred at room temperature for 1 hour, to give a catalyst solution. After the catalyst solution was cooled to a temperature of 0 to 5° C., 1.54 g (10 mmol) of d-citronellal was added dropwise thereto, and the mixture was stirred at a temperature of 0 to 5° C. for 1 hour. After completion of the reaction, 2 ml of water was added thereto, and the organic layer was analyzed by GC. The analysis results are shown below. In the table, conv. represents the conversion rate of d-citronellal, and sel. represents the selectivity for l-isopulegol.

TABLE 2

| Comparative Example | Solvent | (R)-BINOL (eq vs LiAlH₄) | Conv. (%) | Sel. (%) |
|---|---|---|---|---|
| 1 | Toluene | 1.6 eq | 1.35 | 100 |
| 2 | CH₂Cl₂ | 1.6 eq | 1.46 | 100 |
| 3 | Toluene | 2.1 eq | 2.1 | 78.2 |
| 4 | CH₂Cl₂ | 2.1 eq | 1.38 | 100 |

Comparative Example 5

L-Isopulegol Synthesis with Simultaneous Addition of Ligands

In a 50-ml Schlenk flask, 143 mg (0.5 mmol) of (R)-1,1'-bi-2-naphthol and 55.9 mg (0.3 mmol) of 2,2'-biphenol were placed and the air in the flask was replaced with nitrogen gas. Then, 4.6 ml of methylene chloride and 0.5 ml (0.5 mmol) of a toluene solution of triethylaluminum (1.0 mol/L) were successively added thereto and the mixture was stirred at room temperature for 2 hours, to give a catalyst solution. After the catalyst solution was cooled to a temperature of 0 to 5° C., 1.54 g (10 mmol) of d-citronellal was added dropwise thereto, and the mixture was stirred at a temperature of 0 to 5° C. for 1 hour. After completion of the reaction, 2 ml of water was added thereto, and the organic layer was analyzed by GC. According to the analysis results, the substrate conversion rate was 42.3%, the l-isopulegol selectivity was 96.2%, and the ratio of l-isopulegol to the other isomers was 87.2:12.8.

Comparative Example 6

L-Isopulegol Synthesis Using Racemic 1,1'-bi-2-naphthol as Aluminum Catalyst In a 50-ml Schlenk flask, 229 mg (0.8 mmol) of 1,1'-bi-2-naphthol was placed and the air in the flask was replaced with nitrogen gas. Then, 4.6 ml of toluene and 0.5 ml (0.5 mmol) of a toluene solution of triethylaluminum (1.0 mol/L) were successively added thereto and the mixture was stirred at room temperature for 1 hour, to give a catalyst solution. After the catalyst solution was cooled to a temperature of 0 to 5° C., 1.54 g (10 mmol) of d-citronellal was added dropwise thereto, and the mixture was stirred at a temperature of 0 to 5° C. for 1 hour. After completion of the reaction, 2 ml of water was added thereto, and the organic layer was analyzed by GC. According to the analysis results, the substrate conversion rate was 22.7%, the l-isopulegol selectivity was 62.8%, and the ratio of l-isopulegol to the other isomers was 70.2:29.8.

The invention claimed is:

1. An aluminum complex represented by the following general formula (1'):

$$[Al_2(L^1)_n(L^2)_{3-n}]_m \quad (1')$$

wherein in the formula (1'), n represents an integer of 2 or 3; m represents a natural number; $L^1$ represents a ligand represented by the following formula (2'); and $L^2$ represents a ligand represented by the following formula (3'):

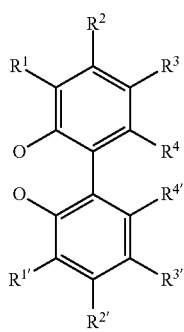

(2')

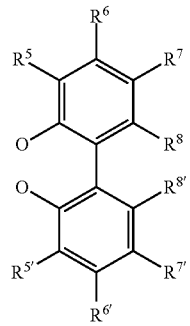

(3')

wherein in the formula (2'), $R^1$, $R^2$, $R^3$, $R^{1'}$, $R^{2'}$ and $R^{3'}$ independently represent a hydrogen atom, a halogen atom, a hydroxyl group, a saturated or unsaturated carbon chain, an optionally substituted aryl group, an optionally substituted heterocyclic group, an alkoxy group, an aryloxy group, an aralkyloxy group, a carboxyl group which may be protected by a protecting group, an amino group, a substituted amino group, a nitro group, an acyl group, a substituted silyl group or a polymer chain; $R^4$ and $R^{4'}$ independently represent a hydroxyl group, a halogen atom, a saturated or unsaturated carbon chain, an optionally substituted aryl group, an optionally substituted heterocyclic group, an alkoxy group, an aryloxy group, an aralkyloxy group, a carboxyl group which may be protected by a protecting group, an amino group, a substituted amino group, an acyl group, a substituted silyl group or a nitro group; and $R^1$ and $R^2$, $R^2$ and $R^3$, $R^3$ and $R^4$, $R^4$ and $R^{4'}$, $R^{4'}$ and $R^{3'}$, $R^{3'}$ and $R^{2'}$, or $R^{2'}$ and $R^{1'}$ may bind to each other to form a ring, and wherein in the formula (3'), $R^5$, $R^6$, $R^7$, $R^8$, $R^{5'}$, $R^{6'}$, $R^{7'}$ and $R^{8'}$ independently represent a hydrogen atom, a hydroxyl group, a halogen atom, a saturated or unsaturated carbon chain, an optionally substituted aryl group, an optionally substituted heterocyclic group, an alkoxy group, an aryloxy group, an aralkyloxy group, a carboxyl group which may be protected by a protecting group, an amino group, a substituted amino group, a nitro group, an acyl group, a substituted silyl group or a polymer chain; and $R^5$ and $R^6$, $R^6$ and $R^7$, $R^7$ and $R^8$, $R^8$ and $R^{8'}$, and $R^7$, $R^{7'}$ and $R^{6'}$, or $R^{6'}$ and $R^{5'}$ may bind to each other to form a ring.

2. The aluminum complex according to claim 1, wherein the ligand represented by the general formula (2') is an optically active compound having a chiral axis.

3. The aluminum complex according to claim 2, wherein both of the ligand represented by the general formula (2') and the ligand compound represented by the general formula (3') are optically active compounds having a chiral axis.

4. A process for preparing an optically active compound, comprising performing, in the presence of an aluminum complex, cyclization of a compound having, in a molecule, a formyl group and a double bond which allow carbonyl-ene cyclization, the compound existing as a mixture of optical isomers thereof, to increase the ratio of a particular optical isomer in a cyclized compound or an unreacted compound, the aluminum complex being obtainable by a reaction of 1 Eq of an aluminum compound represented by the following general formula (1):

$$Al(Lg)_3 \quad (1)$$

wherein in the formula (1), Lg represents an alkyl group, an alkoxy group or a halogen atom, and 1.0 Eq or more of an optically active biaryldiol compound having a chiral axis represented by the following general formula (2):

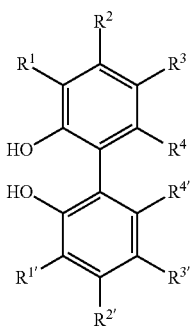

(2)

wherein in the formula (2), $R^1$, $R^2$, $R^3$, $R^{1'}$, $R^{2'}$ and $R^{3'}$ independently represent a hydrogen atom, a halogen atom, a hydroxyl group, a saturated or unsaturated carbon chain, an optionally substituted aryl group, an optionally substituted heterocyclic group, an alkoxy group, an aryloxy group, an aralkyloxy group, a carboxyl group which may be protected by a protecting group, an amino group, a substituted amino group, a nitro group, an acyl group, a substituted silyl group or a polymer chain; $R^4$ and $R^{4'}$ independently represent a hydroxyl group, a halogen atom, a saturated or unsaturated carbon chain, an optionally substituted aryl group, an optionally substituted heterocyclic group, an alkoxy group, an aryloxy group, an aralkyloxy group, a carboxyl group which may be protected by a protecting group, an amino group, a substituted amino group, an acyl group, a substituted silyl group or a nitro group; and $R^1$ and $R^2$, $R^2$ and $R^3$, $R^3$ and $R^4$, $R^4$ and $R^{4'}$, $R^{4'}$ and $R^{3'}$, $R^{3'}$ and $R^{2'}$, or $R^{2'}$ and $R^{1'}$ may bind to each other to form a ring, or by a reaction of 1 Eq of the aluminum compound represented by the above general formula (1), 1.0 to 1.3 Eq of the optically active biaryldiol compound having a chiral axis represented by the above general formula (2) and 0.4 Eq or more of a biaryldiol compound represented by the following general formula (3):

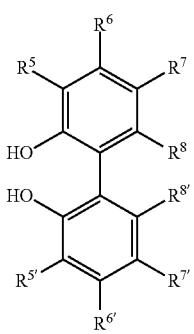

(3)

wherein in the formula (3), $R^5$, $R^6$, $R^7$, $R^8$, $R^{5'}$, $R^{6'}$, $R^{6'}$ and $R^{8'}$ independently represent a hydrogen atom, a hydroxyl group, a halogen atom, a saturated or unsaturated carbon chain, an optionally substituted aryl group, an optionally substituted heterocyclic group, an alkoxy group, an aryloxy group, an aralkyloxy group, a carboxyl group which may be protected by a protecting group, an amino group, a substituted amino group, a nitro group, an acyl group, a substituted silyl group or a polymer chain; and $R^5$ and $R^6$, $R^6$ and $R^7$, $R^7$ and $R^8$, $R^8$ and $R^{8'}$, $R^{8'}$ and $R^{7'}$, $R^{7'}$ and $R^{6'}$, or $R^{6'}$ and $R^{5'}$ may bind to each other to form a ring.

5. The process according to claim 4, wherein the compound having, in a molecule, a formyl group and a double bond which allow carbonyl-ene cyclization is represented by the following general formula (4):

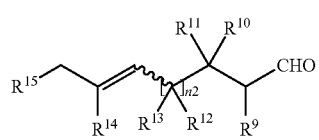

(4)

wherein in the formula (4), n2 represents an integer of 1 or 2; $R^9$, $R^{10}$ and $R^{12}$ independently represent a hydrogen atom or an optionally substituted alkyl group; $R^{11}$ represents an optionally substituted alkyl group or a hydroxyl group which may be protected by a protecting group; $R^{13}$, $R^{14}$ and $R^{15}$ independently represent a hydrogen atom or an optionally substituted alkyl group; and the wavy line represents configuration E or Z.

6. The process according to claim 4, wherein the cyclized compound is represented by the following general formula (5):

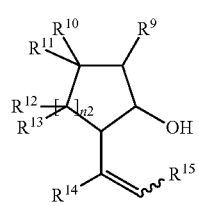

(5)

wherein in the formula (5), n2 represents an integer of 1 or 2; $R^9$, $R^{10}$ and $R^{12}$ independently represent a hydrogen atom or an optionally substituted alkyl group; $R^{11}$ represents an optionally substituted alkyl group or a hydroxyl group which may be protected by a protecting group; $R^{13}$, $R^{14}$ and $R^{15}$ independently represent a hydrogen atom or an optionally substituted alkyl group; and the wavy line represents configuration E or Z.

7. The process according to claim 4, wherein the compound having, in a molecule, a formyl group and a double bond which allow carbonyl-ene cyclization is racemic citronellal or optically active citronellal, and the cyclized compound is optically active isopulegol.

8. The process according to claim 7, wherein the optically active isopulegol is l-isopulegol.

9. The process according to claim 7, wherein the optically active citronellal is l-citronellal.

* * * * *